(12) United States Patent
Katsevich (10) Patent No.: US 7,280,632 B2
(45) Date of Patent: *Oct. 9, 2007

(54) EXACT FILTERED BACK PROJECTION (FBP) ALGORITHM FOR SPIRAL COMPUTER TOMOGRAPHY WITH VARIABLE PITCH

(75) Inventor: Alexander Katsevich, Oviedo, FL (US)

(73) Assignee: University of Central Florida Research Foundation, Inc., Orlando, FL (US)

( * ) Notice: Subject to any disclaimer, the term of this patent is extended or adjusted under 35 U.S.C. 154(b) by 205 days.

This patent is subject to a terminal disclaimer.

(21) Appl. No.: 11/239,605

(22) Filed: Sep. 29, 2005

(65) Prior Publication Data

US 2006/0029180 A1    Feb. 9, 2006

Related U.S. Application Data

(63) Continuation-in-part of application No. 10/523,867, filed as application No. PCT/US04/12536 on Apr. 23, 2004, now Pat. No. 7,197,105, which is a continuation-in-part of application No. PCT/US03/41114, filed on Dec. 24, 2003, which is a continuation-in-part of application No. 10/728,136, filed on Dec. 4, 2003, now Pat. No. 7,010,079, and a continuation-in-part of application No. 10/389,534, filed on Mar. 14, 2003, now Pat. No. 6,804,321, which is a continuation-in-part of application No. 10/389,090, filed on Mar. 14, 2003, now Pat. No. 6,771,733, which is a continuation-in-part of application No. 10/143,160, filed on May 10, 2002, now Pat. No. 6,574,299.

(60) Provisional application No. 60/430,802, filed on Dec. 4, 2002, provisional application No. 60/312,827, filed on Aug. 16, 2001.

(51) Int. Cl.
*A61B 6/03* (2006.01)

(52) U.S. Cl. ............................. 378/15; 378/4; 378/901

(58) Field of Classification Search .................. 378/4, 378/15, 210, 901

See application file for complete search history.

(56) References Cited

U.S. PATENT DOCUMENTS 5,170,439 A    12/1992    Zeng
5,663,995 A    9/1997    Hu
5,706,325 A    1/1998    Hu

(Continued)

*Primary Examiner*—Edward J. Glick
*Assistant Examiner*—John M. Corbett
(74) *Attorney, Agent, or Firm*—Brian S. Steinberger; Phyllis K. Wood; Law Offices of Brian S. Steinberger, P.A.

(57) ABSTRACT

Reconstructing images of objects spirally scanned with two-dimensional detectors with a novel algorithm under a variable pitch (nonconstant speed), where the object is not restricted to moving at a constant velocity. The object can move at variable speeds(increasing, decreasing, combinations thereof) during the scan of the object. The image reconstruction process is proven to create an exact image of the object under the ideal circumstances. The algorithm can have a convolution-based FBP (Filtered Back Projection) structure and works very efficiently. The algorithm uses less computer power and combines the benefits of Exact Algorithms and Approximate algorithms. An object can be moved at a nonconstant speed through a rotating source and oppositely located detector. Additionally, at least one source and oppositely located detector can be mounted on a coil stand for generating the spiral scan.

20 Claims, 9 Drawing Sheets

U.S. PATENT DOCUMENTS

| | | |
|---|---|---|
| 5,784,481 A | 7/1998 | Hu |
| 5,881,123 A | 3/1999 | Tam |
| 5,926,521 A | 7/1999 | Tam |
| 5,960,055 A | 9/1999 | Samarasekera |
| 5,995,580 A | 11/1999 | Schaller |
| 6,009,142 A | 12/1999 | Sauer |
| 6,014,419 A | 1/2000 | Hu |
| 6,072,851 A | 6/2000 | Sivers |
| 6,130,930 A | 10/2000 | Tam |
| 6,148,056 A | 11/2000 | Lin |
| 6,173,032 B1 | 1/2001 | Besson |
| 6,198,789 B1 | 3/2001 | Dafni |
| 6,215,841 B1 | 4/2001 | Hsieh |
| 6,233,303 B1 | 5/2001 | Tam |
| 6,266,388 B1 | 7/2001 | Hsieh |
| 6,292,526 B1 * | 9/2001 | Patch ............................ 378/4 |
| 6,459,754 B1 | 10/2002 | Besson |
| 6,504,892 B1 | 1/2003 | Ning |
| 6,574,299 B1 * | 6/2003 | Katsevich .................... 378/15 |
| 6,771,733 B2 * | 8/2004 | Katsevich ...................... 378/4 |
| 6,804,321 B2 * | 10/2004 | Katsevich ...................... 378/4 |
| 6,898,264 B2 | 5/2005 | Katsevich |
| 2002/0012417 A1 | 1/2002 | Bruder |
| 2002/0015468 A1 | 2/2002 | Kohler |
| 2002/0018540 A1 | 2/2002 | Stierstorfer |
| 2002/0021780 A1 | 2/2002 | Kohler |
| 2002/0025018 A1 | 2/2002 | Takagi |
| 2002/0037068 A1 | 3/2002 | Oikawa |
| 2002/0050970 A1 | 5/2002 | Kajihara |
| 2002/0057756 A1 | 5/2002 | Marume |
| 2004/0223581 A1 | 11/2004 | Katsevich |
| 2006/0039525 A1 * | 2/2006 | Bontus et al. ................. 378/4 |

* cited by examiner

Step 20. Finding families of lines for filtering

Step 21. Choose a discrete set of values of the parameter $s_2$ inside the interval $[s_0 - 2\pi + \Delta, s_0 + 2\pi - \Delta]$.

↓

Step 22. For each selected $s_2$ compute the vector $u(s_0, s_2)$ according to equations (7), (8).

↓

Step 23. For each $u(s_0, s_2)$ computed in Step 22 find a line which is obtained by intersecting the plane through $y(s_0)$ and perpendicular to the said vector $u(s_0, s_2)$ with the detector plane $DP(s_0)$.

↓

Step 24. The collection of lines constructed in Step 23 is the required set of lines (see Fig. 7 which illustrates a family of lines used in the algorithm of the invention).

↓

Step 30

Fig. 9

Step 30. Preparation for filtering

Step 31. Fix a line $L(s_2)$ from the said set of lines obtained in Step 20.

Step 32. Parameterize points on the said line by polar angle $\gamma$ in the plane through $y(s_0)$ and $L(s_2)$.

Step 33. Choose a discrete set of equidistant values $\gamma_j$ that will be used later for discrete filtering in Step 40.

Step 34. For each $\gamma_j$ find the unit vector $\beta_j$ which points from $y(s_0)$ towards the point on $L(s_2)$ that corresponds to $\gamma_j$.

Step 35. Using the CB projection data $D_f(y(q),\Theta)$ for a few values of $q$ close to $s_0$ find numerically the derivative $(\partial/\partial q)D_f(y(q),\Theta)|_{q=s_0}$ for all $\Theta = \beta_j$.

Step 36. Store the computed values of the derivative in computer memory.

Step 37. Repeat Steps 31-36 for all lines $L(s_2)$ identified in Step 20. This way we will create the processed CB data $\Psi(s_0,\beta_j)$

Step 40

Step 50. Back-projection

Step 51. Fix a reconstruction point $x$, which represents a point inside the patient where it is required to reconstruct the image.

Step 52. If $s_0 \in I_{PI}(x)$, then the said filtered CB data affects the image at $x$ and one performs Steps 53-58. If $s_0 \notin I_{PI}(x)$, then the said filtered CB data is not used for image reconstruction at $x$. In this case go back to Step 51 and choose another reconstruction point.

Step 53. Find the projection $\hat{x}$ of $x$ onto the detector plane $DP(s_0)$ and the unit vector $\beta(s_0, x)$, which points from $y(s_0)$ towards $x$.

Step 54. Using equation (9) identify the lines from the said family of lines and points on the said lines that are close to the said projection $\hat{x}$.

Step 55. With interpolation estimate the value of $\Phi(s_0, \beta(s_0, x))$ from the said values of $\Phi(s_0, \beta_j)$ for $\beta_j$ close to $\beta(s_0, x)$.

Step 56. Compute the contribution from the said filtered CB data to the image being reconstructed at the point $x$ by dividing $\Phi(s_0, \beta(s_0, x))$ by $-2\pi^2 |x - y(s_0)|$.

Step 57. Add the said contribution to the image being reconstructed at the point $x$ according to a pre-selected scheme for approximate evaluation of the integral in equation (15).

Step 58. Go to Step 51 and choose a different reconstruction point $x$.

EXACT FILTERED BACK PROJECTION (FBP) ALGORITHM FOR SPIRAL COMPUTER TOMOGRAPHY WITH VARIABLE PITCH

This invention is a Continuation-In-Part of U.S. patent application Ser. No. 10/523,867 filed Feb. 7, 2005, now U.S. Pat. No. 7,197,105 PCT/US04/12536 filed Apr. 23, 2004, PCT/US03/41114 filed Dec. 24, 2003, and Ser. No. 10/728,136, filed Dec. 4, 2003 now U.S. Pat. No. 7,010,079 which claims the benefit of priority to U.S. Provisional Application, Ser. No. 60/430,802 filed, Dec. 4, 2002, and is a Continuation-In-Part of U.S. patent application Ser. No. 10/389,534 filed Mar. 14, 2003 now U.S. Pat. No. 6,804,321, which is a Continuation-In-Part of Ser. No. 10/389,090 filed Mar. 14, 2003 now U.S. Pat. No. 6,771,733. Continuation-In-Part of Ser. No. 10/143,160 filed May 10, 2002 now U.S. Pat. No. 6,574,299, which claims the benefit of priority to U.S. Provisional Application 60/312,827 filed Aug. 16, 2001.

FIELD OF INVENTION

This invention relates to computer tomography, and in particular to processes and systems for reconstructing three dimensional images from the data obtained by a variable pitch spiral scan of an object, such as when the object moves at a variable speed, while the x-ray source rotates around the object.

BACKGROUND AND PRIOR ART

Over the last thirty years, computer tomography (CT) has gone from image reconstruction based on scanning in a slice-by-slice process to spiral scanning. From the 1970s to 1980s the slice-by-slice scanning was used. In this mode the incremental motions of the patient on the table through the gantry and the gantry rotations were performed one after another. Since the patient was stationary during the gantry rotations, the trajectory of the x-ray source around the patient was circular. Pre-selected slices through the patient have been reconstructed using the data obtained by such circular scans.

From the mid 1980s to present day, spiral type scanning has become the preferred process for data collection in CT. Under spiral scanning a table with the patient continuously moves at a constant speed through the gantry that is continuously rotating about the table. At first, spiral scanning has used one-dimensional detectors, which receive data in one dimension (a single row of detectors). Later, two-dimensional detectors, where multiple rows (two or more rows) of detectors sit next to one another, have been introduced. In CT there have been significant problems for image reconstruction especially for two-dimensional detectors. In what follows the data provided by the two-dimensional detectors will be referred to as cone-beam (CB) data or CB projections.

Figure 1:
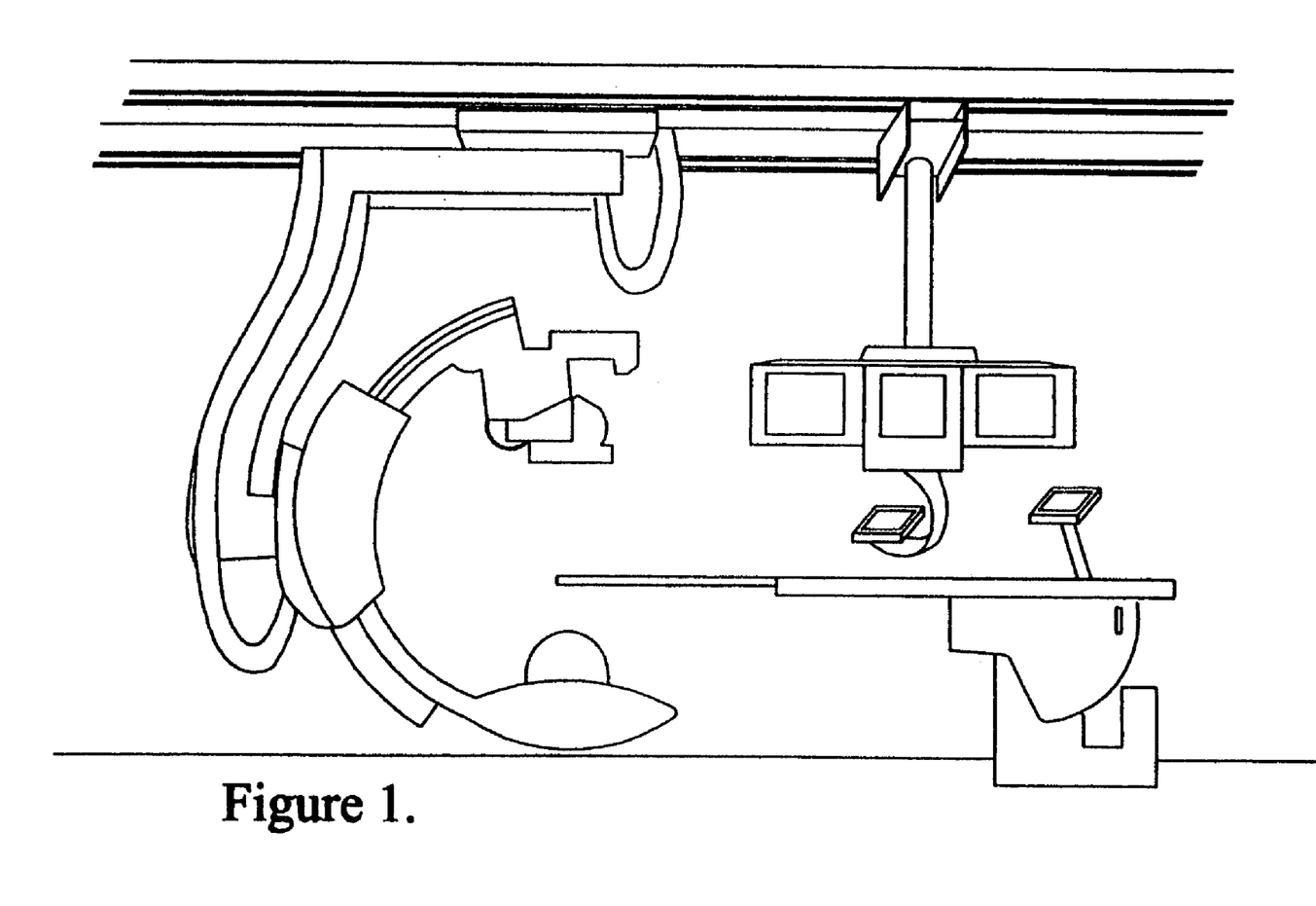
FIG. 1 shows a typical arrangement of a patient on a table that moves within a rotating gantry having an x-ray tube source and a detector array, where cone beam projection data sets are received by the x-ray detector, and an image reconstruction process takes place in a computer with a display for the reconstructed image.

FIG. 1 shows a typical arrangement of a patient on a table that moves at a constant speed within a rotating gantry having an x-ray tube source and a detector array, where cone beam projection data sets are received by the x-ray detector, and an image reconstruction process takes place in a computer with a display for the reconstructed image.

For three-dimensional (also known as volumetric) image reconstruction from the data provided by a spiral scan with two-dimensional detectors, there are two known groups of algorithms: Exact algorithms and Approximate algorithms, that each have known problems. Under ideal circumstances, exact algorithms can provide a replication of an exact image. Thus, one should expect that exact algorithms would produce images of good quality even under non-ideal (that is, realistic) circumstances. However, exact algorithms can be known to take many hours to provide an image reconstruction, and can take up great amounts of computer power when being used. These algorithms can require keeping considerable amounts of cone beam projections in memory. Additionally, some exact algorithms can require large detector arrays to be operable and can have limits on the size of the patient being scanned.

Approximate algorithms possess a filtered back projection (FBP) structure, so they can produce an image very efficiently and using less computing power than Exact algorithms. However, even under the ideal circumstances they produce an approximate image that may be similar to but still different from the exact image. In particular, Approximate algorithms can create artifacts, which are false features in an image. Under certain circumstances these artifacts could be quite severe.

To date, there are no known algorithms that can combine the beneficial attributes of Exact and Approximate algorithms into a single algorithm that is capable of replicating an exact image under the ideal circumstances, uses small amounts of computer power, and reconstructs the exact images in an efficient manner (i.e., using the FBP structure) in the case of variable pitch spiral scanning. Here and everywhere below by the phrase that the algorithm of the invention reconstructs an exact image we will mean that in theory the algorithm is capable of reconstructing an exact image. Since in real life any data contains noise and other imperfections, no algorithm is capable of reconstructing an exact image.

Image reconstruction has been proposed in many U.S. patents. See for example, U.S. Pat. Nos. 5,663,995 and 5,706,325 and 5,784,481 and 6,014,419 to Hu; 5,881,123 and 5,926,521 and 6,130,930 and 6,233,303 to Tam; U.S. Pat. No. 5,960,055 to Samaresekera et al.; U.S. Pat. No. 5,995,580 to Schaller; U.S. Pat. No. 6,009,142 to Sauer; U.S. Pat. No. 6,072,851 to Sivers; U.S. Pat. No. 6,173,032 to Besson; U.S. Pat. No. 6,198,789 to Dafni; U.S. Pat. No. 6,215,841 and 6,266,388 to Hsieh. However, none of the patents overcome all of the deficiencies to image reconstruction referenced above.

SUMMARY OF THE INVENTION

A primary objective of the invention is to provide an improved process and system for reconstructing images of objects that have been scanned in a spiral fashion with variable pitch(at a nonconstant speed) and with two-dimensional detectors.

A secondary objective of the invention is to provide an improved process and system for reconstructing images of objects spirally scanned with variable pitch(at a nonconstant speed) that is known to theoretically be able to reconstruct an exact image and not an approximate image.

A third objective of the invention is to provide an improved process and system for reconstructing images of objects spirally scanned with variable pitch(at a nonconstant speed) that creates an exact image in an efficient manner using a filtered back projection (FBP) structure.

A fourth objective of the invention is to provide an improved process and system for reconstructing images of objects spirally scanned with variable pitch(at a nonconstant speed) that creates an exact image with minimal computer power.

A fifth objective of the invention is to provide an improved process and system for reconstructing images of objects spirally scanned with variable pitch(at a nonconstant speed) that creates an exact image with an FBP structure.

A sixth objective of the invention is to provide an improved process and system for reconstructing images of objects spirally scanned with variable pitch(at a nonconstant speed) that is CB projection driven allowing for the algorithm to work simultaneously with the CB data acquisition.

A seventh objective of the invention is to provide an improved process and system for reconstructing images of objects spirally scanned with variable pitch (at a nonconstant speed) that does not require storing numerous CB projections in computer memory.

An eighth objective of the invention is to provide an improved process and system for reconstructing images of objects spirally scanned with variable pitch (at a nonconstant speed) that allows for almost real time imaging to occur where images are displayed as soon as a slice measurement is completed.

A preferred embodiment of the invention uses a six overall step process for reconstructing the image of an object under a spiral scan. In a first step a current CB projection is measured. Next, a family of lines is identified on a detector according to a novel algorithm. Next, a computation of derivatives between neighboring projections occurs and is followed by a convolution of the derivatives with a filter along lines from the selected family of lines. Next, using the filtered data, the image is updated by performing back projection. Finally, the preceding steps are repeated for each CB projection until an entire object has been scanned. This embodiment works with keeping several (approximately 2-4) CB projections in memory at a time and uses one family of lines.

Unlike the prior art, the invention is not limited to moving an object at a constant speed through a spiral scan. The object can be moved at a nonconstant speed through the gantry.

Other embodiments allow for the object to remain stationary within a spiral coil type stand having multiple x-ray sources and oppositely located detectors arranged along the coil stand which are activated sequentially from different locations on the coil stand. Still furthermore, the entire coil stand with fixed plural x-ray sources and oppositely located detectors rotates all about the object.

Still furthermore, the spiral coil stand can contain a single x-ray source and oppositely located detector which moves along a spiral track about the fixed object at constant and nonconstant speeds. Still furthermore, the spiral stand can include coil links that are not evenly spaced from one another so that the single x-ray source and opposite located detector pass along the length of the object at different speeds. Thus, closely located links allow the single source and detector to pass at a slower rate over an object than distantly spaced apart coil links.

Further objects and advantages of this invention will be apparent from the following detailed description of the presently preferred embodiments, which is illustrated schematically in the accompanying drawings.

DESCRIPTION OF THE PREFERRED EMBODIMENTS

Before explaining the disclosed embodiments of the present invention in detail it is to be understood that the invention is not limited in its application to the details of the particular arrangements shown since the invention is capable of other embodiments. Also, the terminology used herein is for the purpose of description and not of limitation.

FIG. 1 shows a typical arrangement of a patient on a table that moves within a rotating gantry having an x-ray tube source and a detector array, where CB projections are received by the x-ray detector, and an image reconstruction process takes place in a computer 4 with a display 6 for displaying the reconstructed image. For the subject invention, the detector array is a two-dimensional detector array. For example, the array can include two, three or more rows of plural detectors in each row. If three rows are used with each row having ten detectors, then one CB projection set would be thirty individual x-ray detections.

Figure 2:
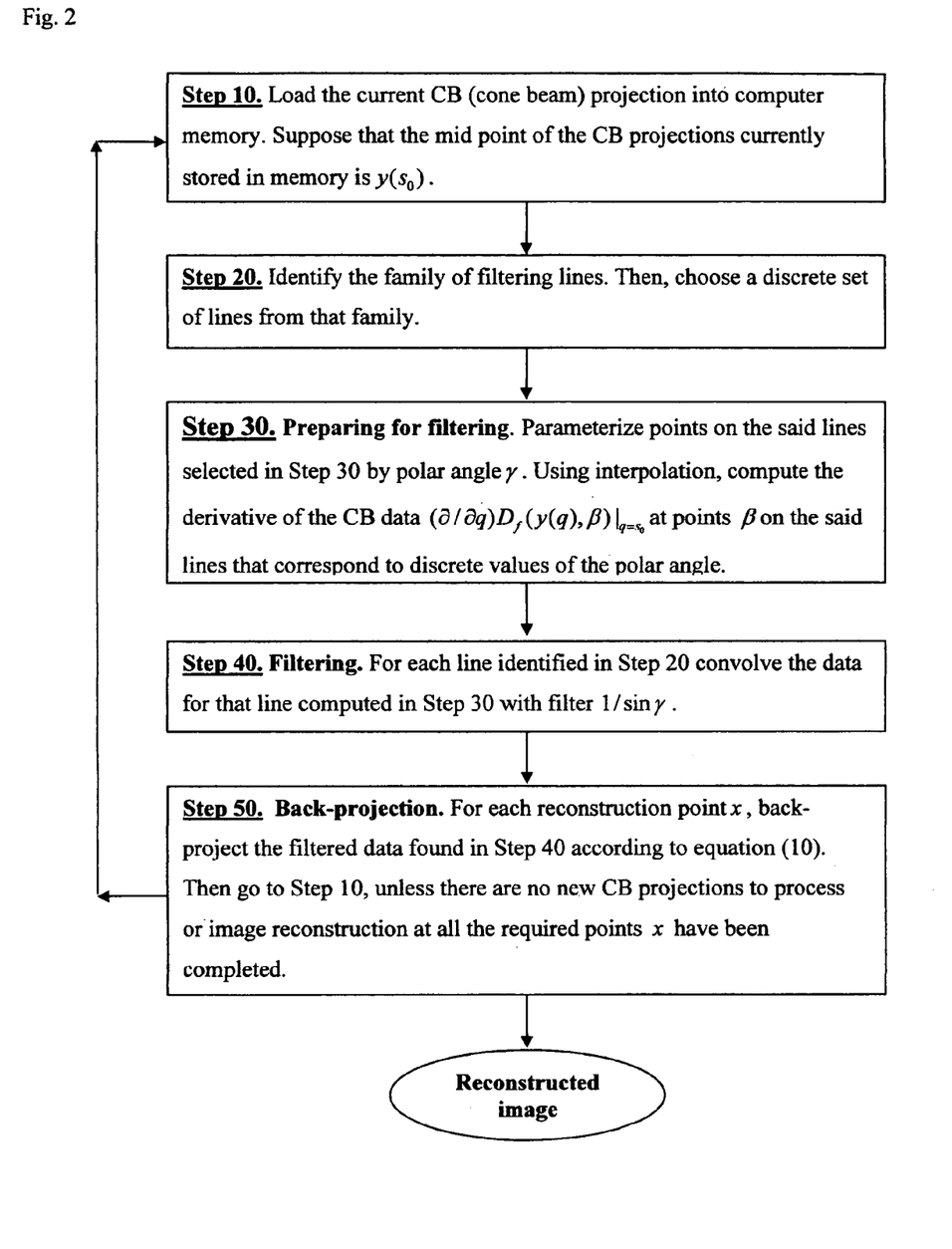
FIG. 2 shows an overview of the basic process steps of the invention.

FIG. 2 shows an overview of the basic process steps of the invention that occur during the image reconstruction process occurring in the computer 4 using a first embodiment.

The first embodiment works with keeping several (approximately 24) CB projections in computer memory at a time and uses one family of lines.

In the first step 10, a current CB projection set is taken. The next step 20 identifies a set of lines on a virtual x-ray detector array according to the novel algorithm, which will be explained later in greater detail. In the given description of the algorithm it is assumed that the detector array is flat, so the selected line can be a straight tilted line across the array.

The next step 30 is the preparation for the filtering step, which includes computations of the necessary derivative of the CB projection data for the selected lines.

The next step 40 is the convolution of the computed derivative (the processed CB data) with a filter along lines from the selected family of lines. This step can also be described as shift-invariant filtering of the derivative of the CB projection data. In the next step 50, the image of the object being computed is updated by performing back projection.

The invention will now be described in more detail by first describing the main inversion formula followed by the novel algorithm.

Unlike the prior art, the invention can be used with objects that move at variable speeds through a rotating gantry. The object can accelerate, decelerate or combinations thereof. A slower speed through the rotating gantry can provide enhanced images of particular portions of an object as desired.

Experimentation in which the speed of the moving table through a rotating gantry was ramped up approximately 25% (twenty five percent) over the course of three (3) gantry rotations was done. Numerical experiments proved the following algorithms worked and demonstrated good image quality and high computational efficiency. Ramping down the speed of the moving table would inherently produce similar results.

Figure 3:
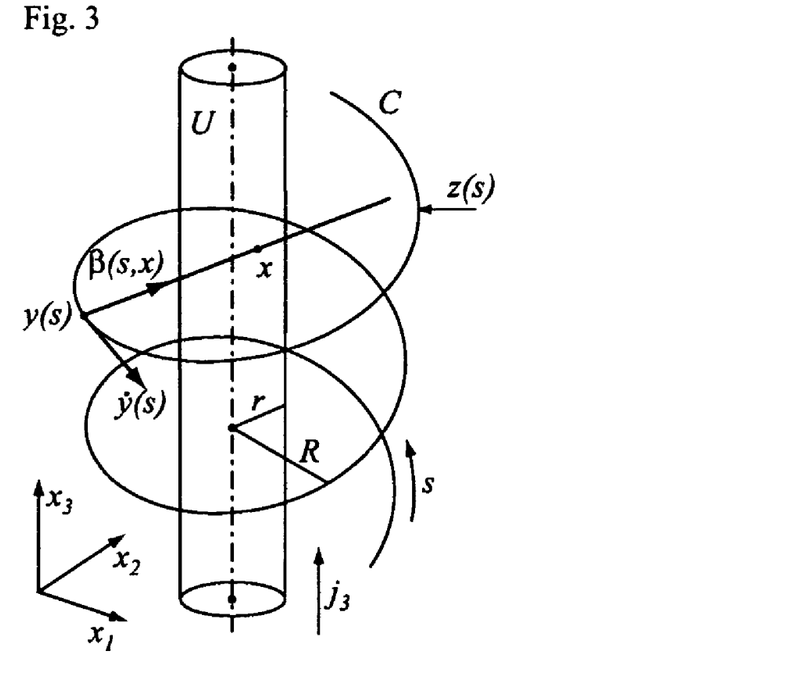
FIG. 3 shows mathematical notations of the spiral scan about the object being scanned.

The variable pitch (variable speed) spiral path C of the x-ray source is described by the following equations and depicted in FIG. 3, which shows mathematical notations of the spiral scan about the object being scanned:

$$y_1(s)=R\cos(s), y_2(s)=R\sin(s), y_3(s)=z(s), \qquad (1)$$

Here s is a real parameter;

z(s) is a function describing the third coordinate of the x-ray source on the spiral; the pitch is variable if z'(s) is not a constant;

R is distance from the x-ray source to the isocenter.

The object being scanned is located inside an imaginary cylinder U of radius r, r<R (see FIG. 3). Let ψ be a smooth function with the properties $$\psi(0)=0; \ 0<\psi'(t)<1, \ t\in[0,2\pi]. \qquad (2)$$

Even though it is not necessary, we will assume in addition that $$\psi'(0)=0.5; \ \psi^{(2k+1)}(0)=0, \ k\geq 1. \qquad (3)$$

Here and in what follows we assume that $s_0$, $s_1$, and $s_2$ are always related by $$s_1=\psi(s_2-s_0)+s_0 \text{ if } s_0\leq s_2<s_0+2\pi, \qquad (4)$$

$$s_1=\psi(s_0-s_2)+s_2 \text{ if } s_0-2\pi<s_2\leq s_0. \qquad (5)$$

Conditions (2) and (3) can be easily satisfied. One can take, for example, ψ(t)=t/2, and this leads to $$s_1=(s_0+s_2)/2, \ s_0-2\pi<s_2<s_0+2\pi. \qquad (6)$$

Denote $$u(s_0, s_2) = \frac{(y(s_1)-y(s_0))\times(y(s_2)-y(s_0))}{|(y(s_1)-y(s_0))\times(y(s_2)-y(s_0))|} sgn(s_2-s_0) \text{ if } 0<|s_2-s_0|<2\pi, \qquad (7)$$

$$u(s_0, s_2) = \frac{\dot{y}(s_0)\times\ddot{y}(s_0)}{|\dot{y}(s_0)\times\ddot{y}(s_0)|} \text{ if } s_2=s_0. \qquad (8)$$

Here $y(s_0)$, $y(s_1)$, $y(s_2)$ are three points on the spiral related according to (4), (5);

$u(s_0, s_2)$ is a unit vector perpendicular to the plane containing the points $y(s_0)$, $y(s_1)$, $y(s_2)$;

$\dot{y}(s):=dy/ds$;

$\ddot{y}(s):=d^2y/ds^2$.

Figure 4:
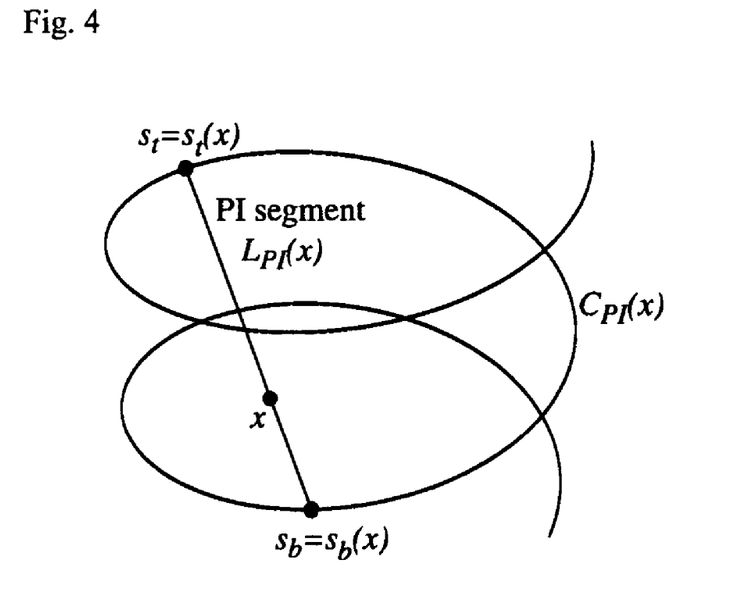
FIG. 4 illustrates a PI segment of an individual image reconstruction point.

Any point strictly inside the spiral belongs to a PI segment. A PI segment is a segment of line endpoints of which are located on the spiral and separated by less than one turn (see FIG. 4). We will assume that such a PI segment is unique. This holds, for example, if z'(s)=const or if z"(s)=const and z'(s) does not change sign or if z'(s)+z'''(s) does not change sign. Let $s=s_b(x)$ and $s=s_t(x)$ denote values of the parameter corresponding to the endpoints of the PI segment containing a reconstruction point x. We will call $I_{PI}(x):=[s_b(x), s_t(x)]$ the PI parametric interval. The part of the spiral corresponding to $I_{PI}(x)$ will be denoted $C_{PI}(x)$ (see FIG. 4 which illustrates a PI segment of an individual image reconstruction point).

Next we fix a reconstruction point x inside the spiral and $s_0\in I_{PI}(x)$. Find $s_2\in I_{PI}(x)$ such that the plane through $y(s_0)$, $y(s_2)$, and $y(s_1(s_0,s_2))$ contains x. More precisely, we have to solve for $s_2$ the following equation $$(x-y(s_0))\cdot u(s_0, s_2)=0, \ s_2\in I_{PI}(x). \qquad (9)$$

Such $s_2$ exists, is unique, and depends smoothly on $s_0$. Therefore, this construction defines $s_2:=s_2(s_0, x)$ and, consequently, $u(s_0,x):=u(s_0,s_2(s_0,x))$. Equation (9) can be solved by a variety of methods, all known under the name "root finders". The main reconstruction formula now is as follows:

$$f(x) = -\frac{1}{2\pi^2}\int_{I_{PI}(x)}\frac{1}{|x-y(s)|}\int_0^{2\pi}\frac{\partial}{\partial q}D_f(y(q), \Theta(s, x, \gamma))\bigg|_{q=s}\frac{d\gamma}{\sin\gamma}ds, \qquad (10)$$

where

ƒ is the function representing the distribution of the x-ray attenuation coefficient inside the object being scanned, $e(s,x)=\beta(s,x)\times u(s,x)$, × is the cross-product of two vectors, $\Theta(s,x,\gamma):=\cos\gamma\beta(s,x)+\sin\gamma e(s,x)$, $D_f$ is the cone beam transform of ƒ:

$$D_f(y,\Theta)=\int_0^\infty f(y+\Theta t)dt, \qquad (11)$$

$$\beta(s, x) := \frac{x-y(s)}{|x-y(s)|}$$

is the unit vector from the focal point y(s) pointing towards the reconstruction point x.

Now we describe an efficient (that is, of the FBP type) implementation of inversion formula (10). It is clear from (9) that $s_2(s,x)$ actually depends only on s and $\beta(s,x)$.

Therefore, we can write $$u(s, \beta) := u(s, s_2(s, \beta)), \ e(s, \beta) := \beta\times u(s, \beta), \ \beta\in S^2, \qquad (12)$$

-continued $$\Psi(s,\beta) := \int_0^{2\pi} \frac{\partial}{\partial q} D_f(y(q), \cos\gamma\beta + \sin\gamma e(s,\beta))\Big|_{q=s} \frac{1}{\sin\gamma} d\gamma,$$

$$f(x) = -\frac{1}{2\pi^2} \int_{I_{Pf}(x)} \frac{1}{|x-y(s)|} \Psi(s, \beta(s,x)) ds. \quad (13)$$

Here $S^2$ is the unit sphere.

Figure 5:
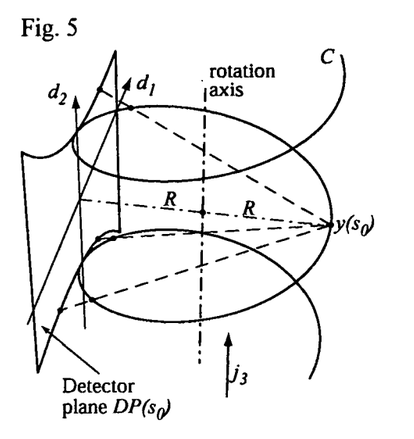
FIG. 5 illustrates a stereographic projection from the current source position on to the detector plane used in the algorithm for the invention.

To better understand equations (12), (13), we illustrate various important features on the detector array. Suppose first that the x-ray source is fixed at y(s) for some $s \in I_{Pf}(x)$. Project stereographically the upper and lower turns of the spiral onto the detector plane as shown in FIG. 5 which illustrates a stereographic projection from the current source position on to the detector plane used in the algorithm for the invention.

Figure 6:
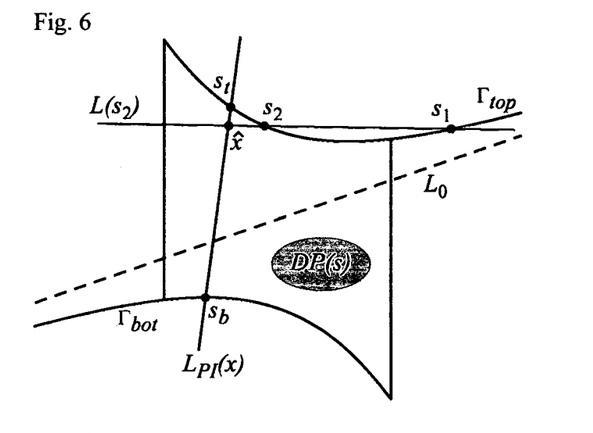
FIG. 6 illustrates various lines and curves, such as boundaries, on the detector plane.
Figure 7:
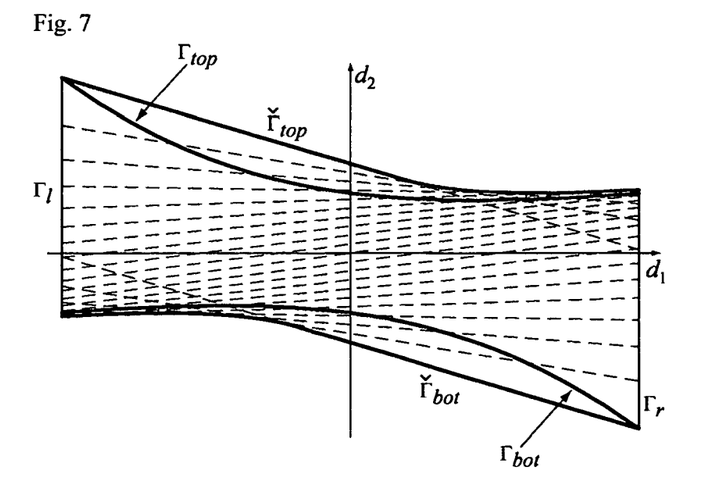
FIG. 7 illustrates a family of lines used in the algorithm of the invention.

Since the detector array rotates together with the source, the detector plane depends on s and is denoted DP(s). It is assumed that DP(s) is parallel to the axis of the spiral and is tangent to the cylinder $y_1^2 + y_2^2 = R^2$ (cf. equation (1)) at the point opposite to the source. Thus, the distance between y(s) and the detector plane is 2R. Introduce coordinates in the detector plane as follows. Let the $d_1$-axis be perpendicular to the axis of the spiral, and the $d_2$-axis—parallel to it. This gives the following parametric curves:

$$d_1(q) = 2R \frac{\sin(q-s)}{1-\cos(q-s)}, \quad d_2(q) = 2 \frac{z(q)-z(s)}{1-\cos(q-s)}, \quad (14)$$

$$\Delta \le q-s \le 2\pi-\Delta \text{ or } \Delta-2\pi \le q-s \le -\Delta,$$

where $\Delta$ is determined by the radius r of the imaginary cylinder U inside which the patient is located (see FIG. 3): $\Delta = 2\cos^{-1}(r/R)$. The top and bottom curves are denoted $\Gamma_{top}$ and $\Gamma_{bot}$, respectively (see FIG. 6 which illustrates various lines and curves, such as boundaries, on the detector plane). The common asymptote of $\Gamma_{top}$ and $\Gamma_{bot}$ is denoted $L_0$. Let $\hat{x}$ denote the projection of x. Since $s \in I_{Pf}(x)$, $\hat{x}$ is projected into the area between $\Gamma_{top}$ and $\Gamma_{bot}$ (see FIG. 6). Fix $s_2 \in [s-2\pi+\Delta, s+2\pi-\Delta]$, $s_2 \ne s$, and let $\Pi(s_2)$ denote the plane through y(s),y($s_2$), and y($s_1(s,s_2)$). If $s_2=s$, $\Pi(s_2)$ is determined by continuity and coincides with the plane through y(s) and parallel to $\dot{y}(s), \ddot{y}(s)$. The family of lines $L(s_2)$ obtained by intersecting $\Pi(s_2)$ with the detector plane is shown in FIG. 7.

The main assumption under which equation (10) holds is that the curves $\Gamma_{top}$ and $\Gamma_{bot}$ are convex. This happens, for example, if z'(s)=const or if z"(s)=const and z'(s) does not change sign or if z'(s)+z'''(s) does not change sign.

By construction, given any $x \in U$ with $\beta(s,x)$ parallel to $\Pi(s_2)$ and such that $\hat{x}$ appears to the left (right) of the point of where the line $L(s_2)$ intersects $\Gamma_{top}$ ($\Gamma_{bot}$) for the first time if $\hat{x}$ is above (below) $L_0$, $s_2$ used here is precisely the same as $s_2$ found by solving (9). The condition that we have formulated regarding the location of $\hat{x}$ relative to $s_2$ and $L_0$ guarantees that $s_2 \in I_{Pf}(x)$. Since $e(s,\beta)\cdot\beta=0, |e(s,\beta)|=1$, we can write:

$$\beta = (\cos\theta, \sin\theta); \ e(s,\beta) = -\sin\theta, \cos\theta); \ \beta, e(s,\beta) \in \Pi(s_2). \quad (15)$$

Therefore, $$\Psi(s,\beta) = \int_0^{2\pi} \frac{\partial}{\partial q} D_f(y(q), (\cos(\theta+\gamma), \sin(\theta+\gamma)))\Big|_{q=s} \frac{1}{\sin\gamma} d\gamma, \quad (16)$$

$$\beta \in \Pi(s_2).$$

Equation (16) is of convolution type and one application of Fast Fourier Transform (FFT) gives values of $\Psi(s,\beta)$ for all $\beta \in \Pi(s_2)$ at once.

Equations (13) and (16) would represent that the resulting algorithm is of the FBP type. This means that processing of every CB projection consists of two steps. First, shift-invariant and x-independent filtering along a family of lines on the detector is performed. Second, the result is back-projected to update the image matrix. The main property of the back-projection step is that for any point $\hat{x}$ on the detector the value obtained by filtering at $\hat{x}$ is used for all points x on the line segment connecting the current source position y(s) with $\hat{x}$. Since $\partial/\partial q$ in (16) is a local operation, each CB projection is stored in memory as soon as it has been acquired for a short period of time for computing this derivative at a few nearby points and is never used later.

Now we describe the algorithm in detail following the six steps 10-60 shown in FIG. 2.

Step 10. Load the current CB(cone beam) projection into computer memory. Suppose that the mid point of the CB projections currently stored in memory is y($s_0$). The detector plane corresponding to the x-ray source located at y($s_0$) is denoted DP($s_0$).

Figure 8:
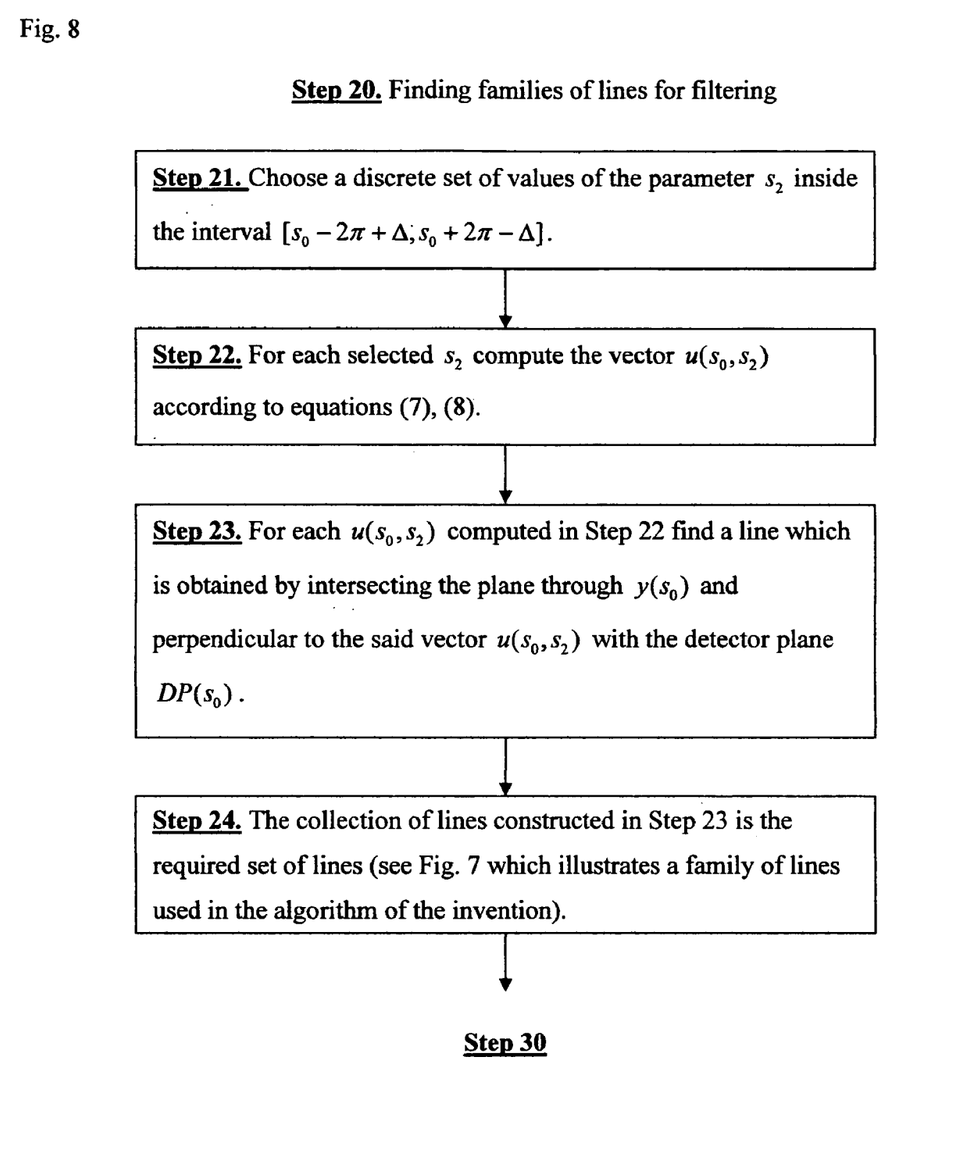
FIG. 8 is a four substep flow chart for identifying the set of lines, which corresponds to step 20 of FIG. 2.

Step 20. FIG. 8 is a four substep flow chart for identifying the set of lines, which corresponds to step 20 of FIG. 2. Referring to FIG. 8, the set of lines can be selected by the following substeps 21, 22, 23 and 24.

Step 21. Choose a discrete set of values of the parameter $s_2$ inside the interval [$s_0-2\pi+\Delta, s_0+2\pi-\Delta$].

Step 22. For each selected $s_2$ compute the vector u($s_0, s_2$) according to equations (7), (8).

Step 23. For each u($s_0,s_2$) computed in Step 22 find a line which is obtained by intersecting the plane through y($s_0$) and perpendicular to the said vector u($s_0,s_2$) with the detector plane DP($s_0$).

Step 24. The collection of lines constructed in Step 23 is the required set of lines (see FIG. 7 which illustrates a family of lines used in the algorithm of the invention).

Figure 9:
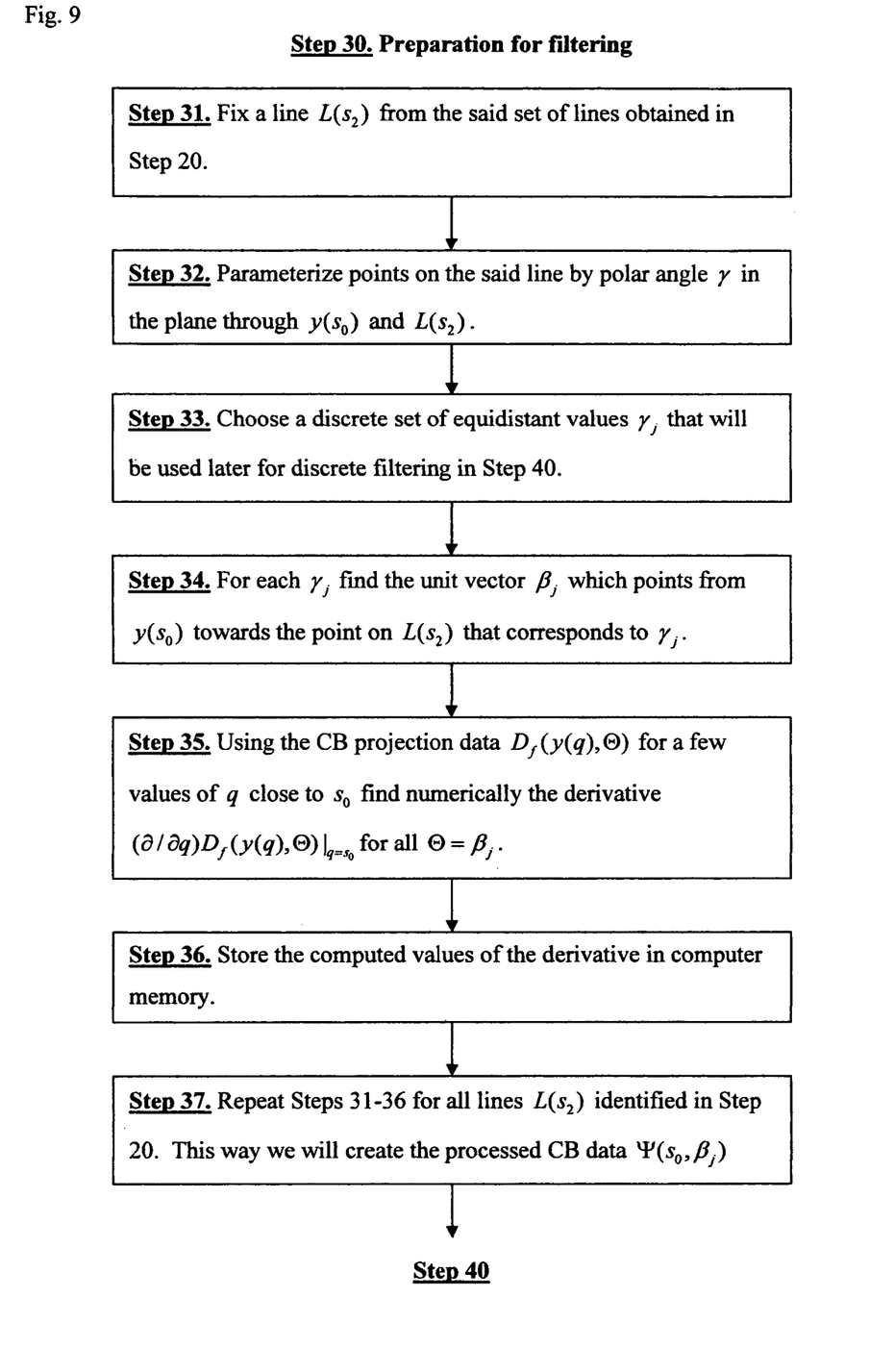
FIG. 9 is a seven substep flow chart for preparation for filtering, which corresponds to step 30 of FIG. 2.

Step 30. Preparation for filtering corresponds to step 30 of FIG. 2, which will now be described.

Step 31. Fix a line L($s_2$) from the said set of lines obtained in Step 20.

Step 32. Parameterize points on the said line by polar angle $\gamma$ in the plane through y($s_0$) and L($s_2$).

Step 33. Choose a discrete set of equidistant values $\gamma_j$ that will be used later for discrete filtering in Step 40.

Step 34. For each $\gamma_j$ find the unit vector $\beta_j$ which points from y($s_0$) towards the point on L($s_2$) that corresponds to $\gamma_j$.

Step 35. Using the CB projection data $D_f(y(q), \Theta)$ for a few values of q close to $s_0$ find numerically the derivative $(\partial/\partial q)D_f(y(q), \Theta)|_{q=s_0}$ for all $\Theta=\beta_j$.

Step 36. Store the computed values of the derivative in computer memory.

Step 37. Repeat Steps 31-36 for all lines $L(s_2)$ identified in Step 20. This way we will create the processed CB data $\Psi(s_0,\beta_j)$ corresponding to the x-ray source located at $y(s_0)$.

Step 40. Filtering

Figure 10:
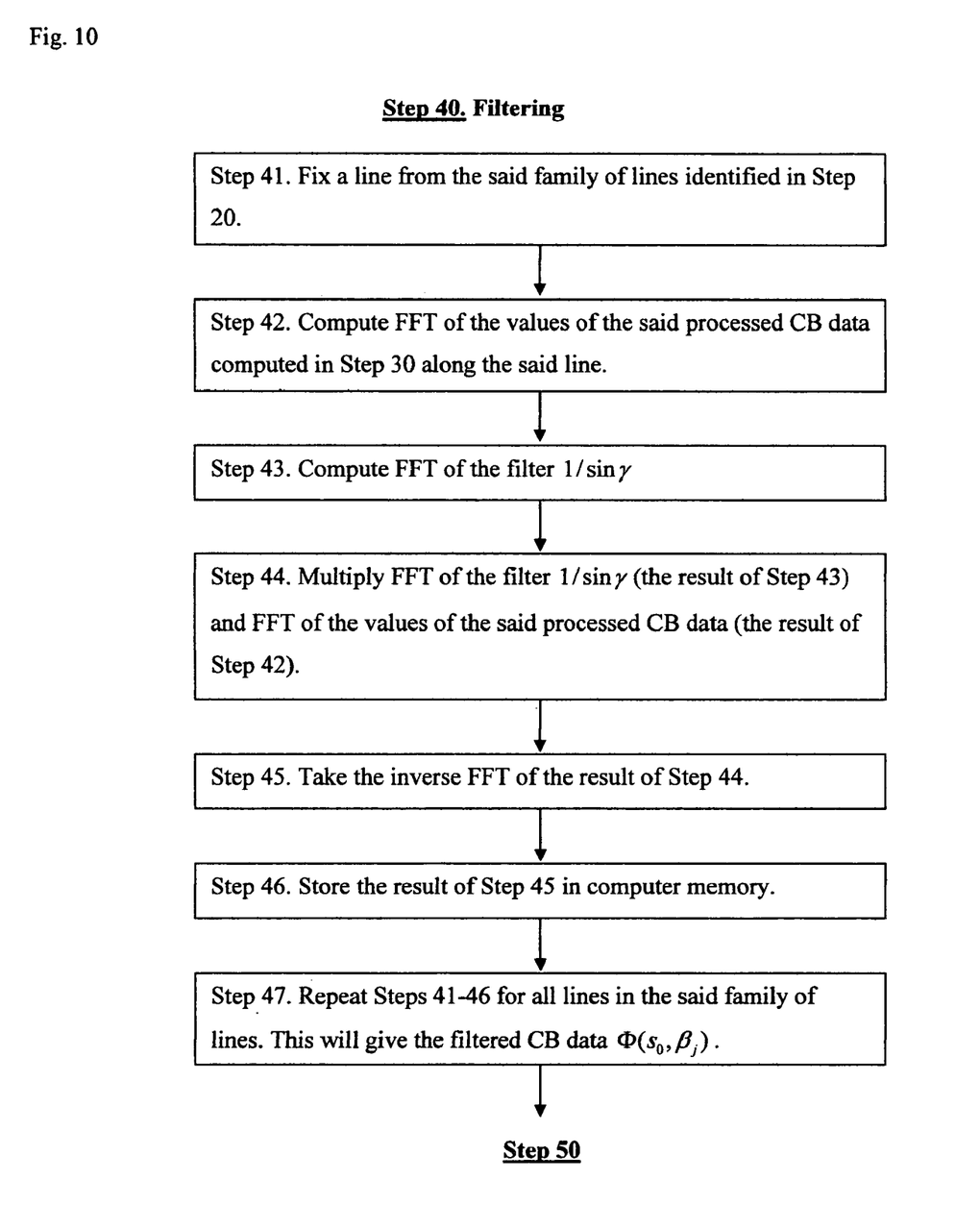
FIG. 10 is a seven substep flow chart for filtering, which corresponds to step 40 of FIG. 2.

FIG. 10 is a seven substep flow chart for filtering, which corresponds to step 40 of FIG. 2, which will now be described.

Step 41. Fix a line from the said family of lines identified in Step 20. Step 42. Compute FFT of the values of the said processed CB data computed in Step 30 along the said line.

Step 43. Compute FFT of the filter $1/\sin \gamma$

Step 44. Multiply FFT of the filter $1/\sin \gamma$ (the result of Steps 43) and FFT of the values of the said processed CB data (the result of Steps 42).

Step 45. Take the inverse FFT of the result of Step 44.

Step 46. Store the result of Step 45 in computer memory.

Step 47. Repeat Steps 41-46 for all lines in the said family of lines. This will give the filtered CB data $\Phi(s_0, \beta_j)$.

By itself the filtering step is well known in the field and can be implemented, for example, as shown and described in U.S. Pat. No. 5,881,123 to Tam, which is incorporated by reference.

Step 50. Back-projection

Figure 11:
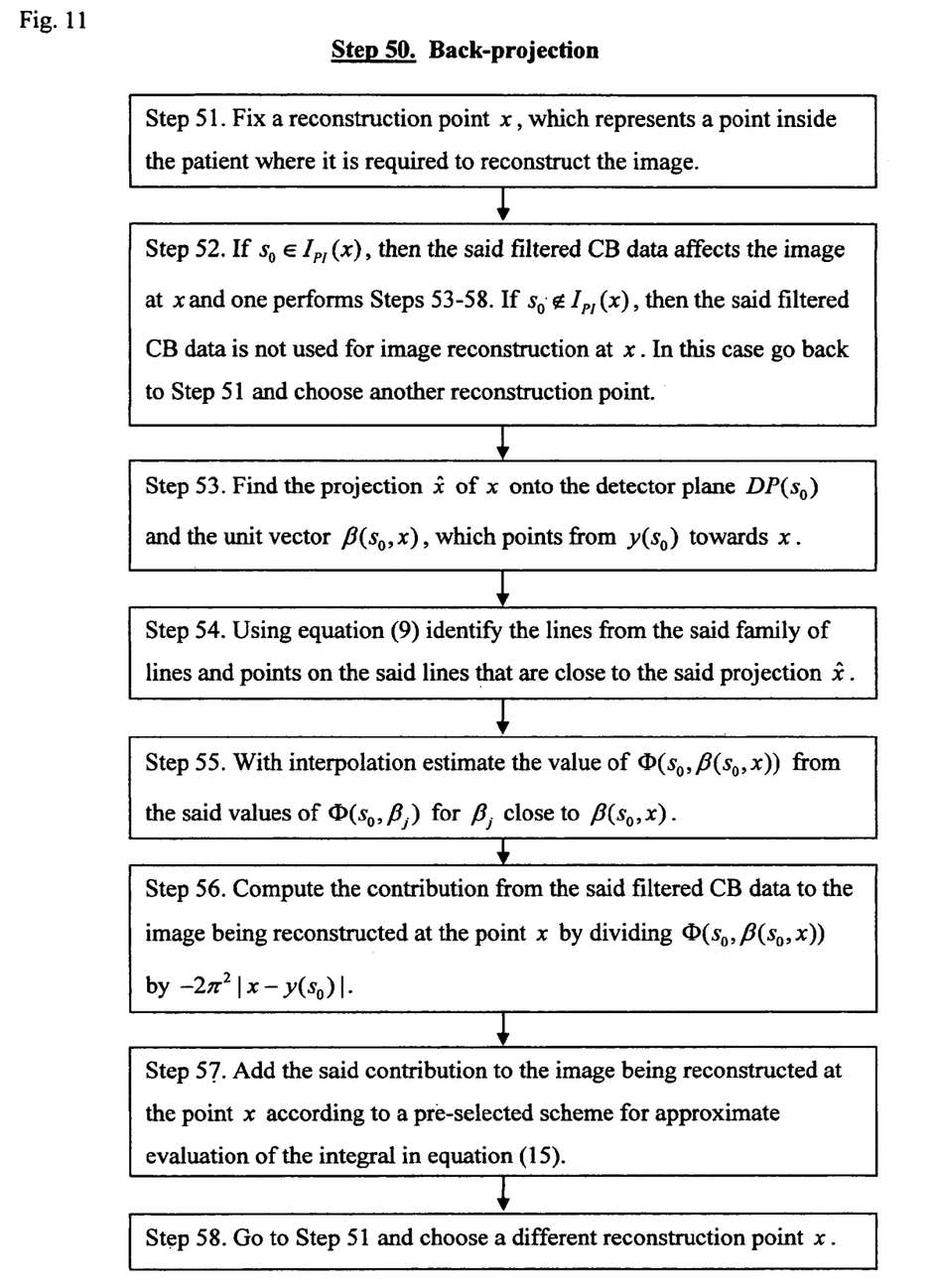
FIG. 11 is an eight substep flow chart for backprojection, which corresponds to step 50 of FIG. 2.

FIG. 11 is an eight substep flow chart for backprojection, which corresponds to step 50 of FIG. 2, which will now be described.

Step 51. Fix a reconstruction point x, which represents a point inside the patient where it is required to reconstruct the image.

Step 52. If $s_0$ belongs to $I_{PI}(x)$, then the said filtered CB data affects the image at x and one performs Steps 53-58. If $s_0$ is not inside the interval $I_{PI}(x)$, then the said filtered CB data is not used for image reconstruction at x. In this case go back to Step 51 and choose another reconstruction point.

Step 53. Find the projection $\hat{x}$ of x onto the detector plane $DP(s_0)$ and the unit vector $\beta(s_0,x)$, which points from $y(s_0)$ towards x.

Step 54. Using equation (9) identify the lines from the said family of lines and points on the said lines that are close to the said projection $\hat{x}$. This will give a few values of $\Phi(s_0,\beta_j)$ for $\beta_j$ close to $\beta(s_0,x)$.

Step 55. With interpolation estimate the value of $\Phi(s_0, \beta(s_0,x))$ from the said values of $\Phi(s_0,\beta_j)$ for $\beta_j$ close to $\beta(s_0,x)$.

Step 56. Compute the contribution from the said filtered CB data to the image being reconstructed at the point x by dividing $\Phi(s_0,\beta(s_0,x))$ by $-2\pi^2|x-y(s_0)|$.

Step 57. Add the said contribution to the image being reconstructed at the point x according to a pre-selected scheme (for example, the Trapezoidal scheme) for approximate evaluation of the integral in equation (15).

Step 58. Go to Step 51 and choose a different reconstruction point x.

Step 60. Go to Step 10 (FIG. 2) and load the next CB projection into computer memory. The image can be displayed at all reconstruction points x for which the image reconstruction process has been completed (that is, all the subsequent CB projections are not needed for reconstructing the image at those points). Discard from the computer memory all the CB projections that are not needed for image reconstruction at points where the image reconstruction process has not completed. The algorithm concludes when the scan is finished or the image reconstruction process has completed at all the required points.

Figure 12:
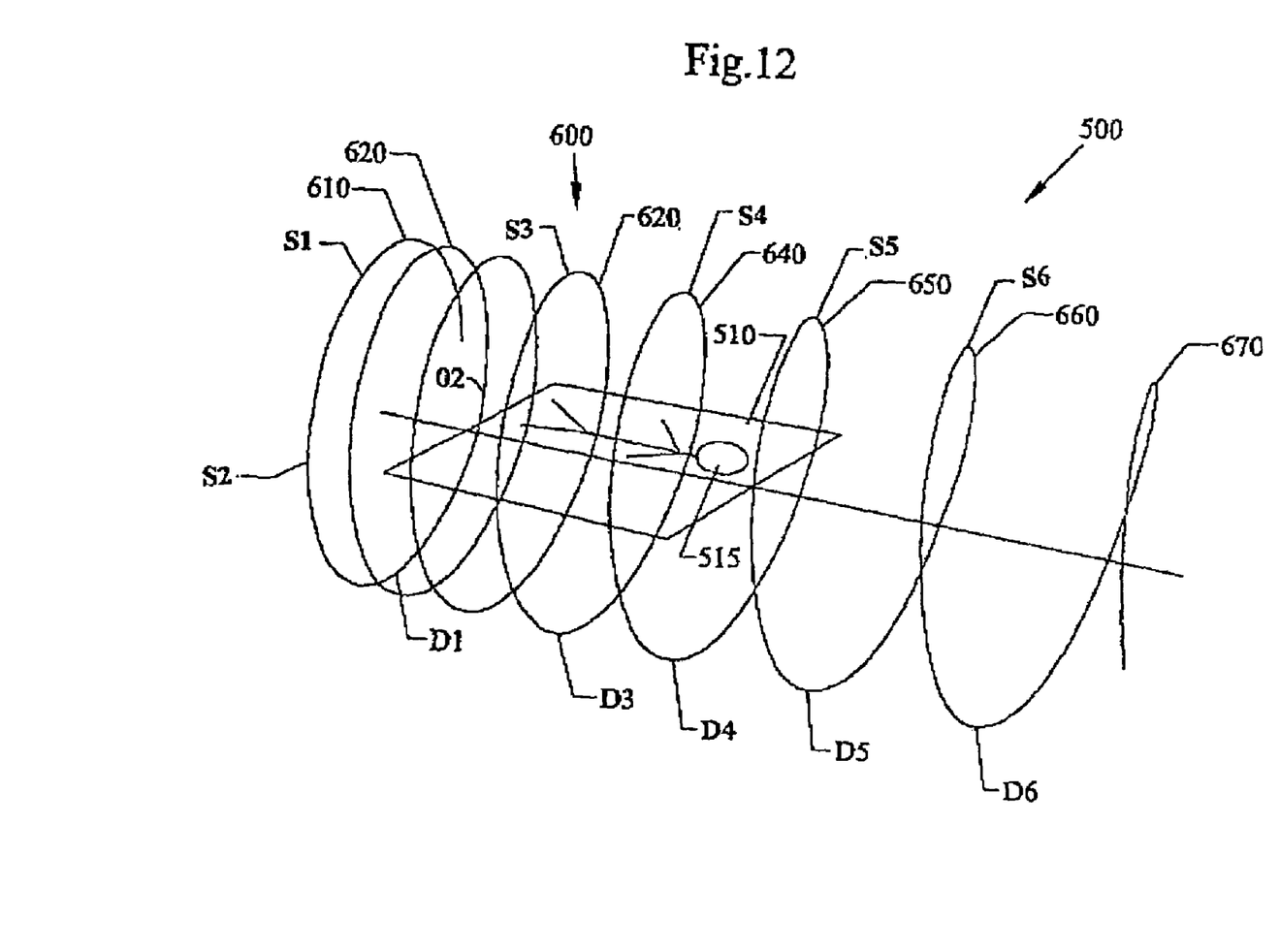
FIG. 12 shows an arrangement of scanning an object with a spiral coil x-ray source where the object being scanned remains stationary inside.

The invention can work with other types of variable pitch(nonconstant speed) spiral scans. FIG. 12 shows an arrangement 500 of scanning an object 515 such as a human body, on a stationary table 510 within a spiral coil stand the object 515 being scanned remains stationary inside. The coil stand can be located inside of a chamber, or be a virtual coil stand within a chamber. As previously described, unlike the prior art, the invention is not limited to moving an object at a constant speed through a spiral scan. The object 515 can remain stationary within a stationary spiral coil type stand, where multiple x-ray sources S1, S2, S3, S4, S5, S6 and oppositely located detectors D1, D2, D3, D4, D5, D6 arranged along the stationary coil stand 600 emit x-rays in a sequential manner about the stationary object 515 such as from right to left, left to right, the middle to the left, the middle to the right, and combinations thereof, to generate a spiral scan Still furthermore, the coil stand 600 can have fixed multiple x-ray sources and detectors so that the entire coil stand 600 can rotate about the object 515, and generate a spiral scan.

Still furthermore, the spiral coil stand 600 can contain a single x-ray source S1 and oppositely located detector D1 which moves along a spiral track on the stand 600 about the fixed object 510 at constant and nonconstant speeds. Still furthermore, the spiral stand 600 can include coils links 610, 620, 630, 640, 650, 660, 670 that are not evenly spaced from one another so that the single x-ray source S1 and opposite located detector D1 moving at a constant speed ends up passing along the length of the object 515 at different speeds. Thus, closely located links 610, 620 allow the single source S1 and detector D1 to pass at a slower rate over an object than distantly spaced apart coil links 650, 660, 670.

The spiral coil stand embodiments described above can also work with constant pitch(constant speed) applications.

Other Embodiments of the invention are possible. For example, one can integrate by parts in equation (10) as described in the inventor's previous U.S. patent application Ser. No. 10/143,160 filed May 10, 2002 now U.S. Pat. No. 6,574,299, now incorporated by reference, to get an exact FBP-type inversion formula which requires keeping only one CB projection in computer memory. The algorithmic implementation of this alternative embodiment can be similar to and include the algorithmic implementation of Embodiment Two in the inventor's previous U.S. patent application Ser. No. 10/143,160 filed May 10, 2002 now U.S. Pat. No. 6,574,299, now incorporated by reference.

Although the preferred embodiments describe applications of using x-ray sources for creating data for image reconstruction, the invention can be applicable with other sources such as but not limited to early arriving photons that create line integral data for image reconstruction.

While the invention has been described, disclosed, illustrated and shown in various terms of certain embodiments or modifications which it has presumed in practice, the scope of the invention is not intended to be, nor should it be deemed to be, limited thereby and such other modifications or embodiments as may be suggested by the teachings herein are particularly reserved especially as they fall within the breadth and scope of the claims here appended.

I claim:

1. A method of reconstructing images from data provided by at least one detector, comprising the steps of:
    variable pitch spiral scanning an object with at least one detector with at least one cone beam projection source; and reconstructing an exact image of the scanned object in an efficient manner with a convolution based FBP (Filtered Back Projection) algorithm.

2. The method of claim 1, wherein the scanning step further includes the step of: moving a table supporting the object through a rotational scanner with non-constant speed.

3. The method of claim 1, wherein the step of reconstructing further includes the step of:
shift invariant filtering of the cone beam projections; and
back projection updating the image of the scanned object.

4. The method of claim 1, wherein the step of reconstructing includes the steps of:
storing approximately 2 to approximately 4 cone beam (CB) projections in memory at a time; and
using one family of lines for the step of reconstructing.

5. The method of claim 1, wherein the step of reconstructing includes the steps of:
storing 1 cone beam (CB) projection in memory at a time; and
using one family of lines for the step of reconstructing.

6. The method of claim 1, wherein the scanning step further includes the step of:
supporting the object in a stationary position within a coil stand; and
moving the one source and the one detector along the coil stand about the object at a constant speed to generate a spiral scan.

7. The method of claim 1, wherein the scanning step further includes the step of:
supporting the object in a stationary position within a coil stand; and
moving the one source and the one detector along the coil stand about the object at a nonconstant speed to generate a spiral scan.

8. The method of claim 1, wherein the scanning step further includes the step of:
supporting the object in a stationary position within a coil stand; and
placing plural sources and oppositely located detectors on the coil stand about the object; and
sequentially activating the cone beam projections to generate a spiral scan.

9. The method of claim 1, wherein the scanning step further includes the step of:
supporting the object in a stationary position within a coil stand; and
placing plural sources and oppositely located detectors on the coil stand about the object; and
rotating the coil stand about the object to generate a spiral scan.

10. A method of computing images derived from a variable pitch spiral computer tomography with detectors, comprising the steps of:
(a) collecting cone beam (CB) data from a detector during a variable pitch spiral scan of an object;
(b) identifying lines on a plane Π intersecting the cone beam, wherein the step (b) of identifying lines includes the steps of:
(bi) choose a discrete set of values of a parameter $s_2$ inside an interval containing $s_0$, where $s_0$ and $s_2$ are values of the parameter along the spiral;
(bii) compute a vector $u(s_0, s_2)$ for each selected $s_2$ according to equations $$u(s_0, s_2) = \frac{(y(s_1) - y(s_0)) \times (y(s_2) - y(s_0))}{|(y(s_1) - y(s_0)) \times (y(s_2) - y(s_0))|} sgn(s_2 - s_0)$$

when $0 < |s_2 - s_0| < 2\pi$, $$u(s_0, s_2) = \frac{\dot{y}(s_0) \times \ddot{y}(s_0)}{|\dot{y}(s_0) \times \ddot{y}(s_0)|} \text{ when } s_2 = s_0,$$

where, $y(s_0)$, $y(s_1)$, $y(s_2)$ are three points on the spiral related according to the following equations $s_1 = \Psi(s_2 - s_0) + s_0$ when $s_0 \leq s_2 < s_0 + 2\pi$, $s_1 = \Psi(s_0 - s_2) + s_2$ when $s_0 - 2\pi < s_2 \leq s_0$, and $\Psi$ is a function with the properties $\Psi(0)=0$; $0<\Psi'(t)<1$, $t\in[0, 2\pi]$;
$u(s_0, s_2)$ is a unit is a unit vector perpendicular to the plane containing the points $y(s_0)$, $y(s_1)$, $y(s_2)$;
$\dot{y}(s) := dy/ds$;
$\ddot{y}(s) := d^2y/ds^2$;
(biii) find a line for each $u(s_0, s_2)$ which is obtained by intersecting the plane through $y(s_0)$ and perpendicular to the said vector $u(s_0, s_2)$ with the plane Π; and
(biv) repeating steps (bi-biii), and forming a family of lines from a collection of the lines;
(c) preprocessing and shift invariant filtering said data along said lines;
(d) back projecting said filtered data to form a precursor of said image; and
(e) repeating steps a, b, c, and d until an exact image of the object is completed.

11. The method of claim 10, wherein the scan includes an x-ray exposure of the object.

12. The method of claim 10, further including the step of (b5) preparing the data prior to the step (c) filtering step of:
(b5i) fixing a line $L(s_2)$ from the set of lines obtained in step (b);
(b5ii) parameterizing points on the lines by polar angle $\gamma$ in the plane through $y(s_0)$ and $L(s_2)$;
(b5iii) choosing a discrete set of equidistant values $\gamma_j$;
(b5iv) find the unit vector $\beta_j$ for each $\gamma_j$ which points from $y(s_0)$ towards the point on $L(s_2)$ that corresponds to $\gamma_j$;
(b5v) compute derivatives using the CB projection data $D_f(y(q),\Theta)$ for a few values of q close to $s_0$ using equation $(\partial/\partial q)D_f(y(q),\Theta)|_{q=s_0}$ for all $\Theta=\beta_j$;
(b5vi) store the computed derivatives; and
(b5vii) repeat steps (b5i) to b5vi for all lines $L(s_2)$ identified step (b), in order to create processed CB data $\Psi(s_0, \beta_j)$ corresponding to an x-ray source located at $y(s_0)$.

13. The method of claim 10, wherein the back-projection step (d) includes the steps of:
(di) fix a reconstruction point x, which represents a point inside the object being scanned where it is required to reconstruct the image;
(dii) when $s_0$ belongs to $I_{Pf}(x)$, then the said filtered CB data affects the image at x and one performs Steps (diii) to (dviii), when $s_0$ is not inside interval $I_{Pf}(x)$, then the said filtered CB data is not used for image reconstruction at x and go back to step (di) and choose another reconstruction point, wherein $I_{Pf}(x):=[s_b(x),s_t(x)]$ is the PI parametric interval where $s=s_b(x)$ and $s=s_t(x)$ denote values of the parameter corresponding to the endpoints of the PI segment containing the construction point x;

(diii) find a projection $\hat{x}$ of x onto a detector plane $DP(s_0)$ and unit vector $\beta(s_0, x)$, which points from $y(s_0)$ towards x;

(div) identify lines from family of lines and points on the said lines that are close to the said projection $\hat{x}$, using equation $(x-y(s_0)) \cdot u(s_0, s_2)=0, s_2 \epsilon I_{PI}(x)$;

(dv) using interpolation find value of $\Phi(s_0,\beta(s_0,x))$ from $\Phi(s_0,\beta_j)$ for $\beta_j$ close to $\beta(s_0,x)$;

(dvi) compute contribution from filtered CB data to the image being reconstructed at the point x by dividing $\Phi(s_0, \beta(s_0,x))$ by $-2\pi^2|x-y(s_0)|$;

(dvii) add the contribution to the image being reconstructed at the point x according to a pre-selected scheme; and (dviii) go to step (di) and choose a different reconstruction point x.

14. The method of claim 10, further comprising the steps of:

storing approximately 2 to approximately 4 cone beam (CB) projections in memory at a time; and using one family of lines for the step of reconstructing.

15. The method of claim 10, further comprising the steps of:

storing 1 cone beam CB projection in memory at a time; and using one family of lines for reconstructing the exact image.

16. The method of claim 10, further comprising the step of:

moving the object at a nonconstant speed through a rotating source and oppositely located detector to generate the variable pitch spiral scan.

17. The method of claim 10, further comprising the step of:

positioning the object in a stationary position within a coil stand; and generating the spiral scan from at least one source and at least one oppositely located detector located on the coil stand.

18. A method of identifying lines on a plane Π used for reconstructing images based on a variable pitch spiral scan of an object in a computer tomography system, comprising the steps of:

(i) choose a discrete set of values of a parameter $s_2$ inside an interval containing $s_0$, where $s_0$ and $s_2$ are values of the parameter along the spiral scan path;

(ii) compute a vector $u(s_0, s_2)$ for each selected $s_2$ according to equations $$u(s_0, s_2) = \frac{(y(s_1) - y(s_0)) \times (y(s_2) - y(s_0))}{|(y(s_1) - y(s_0)) \times (y(s_2) - y(s_0))|} sgn(s_2 - s_0)$$

when $0 < |s_2 - s_0| < 2\pi$, $$u(s_0, s_2) = \frac{\dot{y}(s_0) \times \ddot{y}(s_0)}{|\dot{y}(s_0) \times \ddot{y}(s_0)|} \text{ when } s_2 = s_0,$$

where, $y(s_0)$, $y(s_1)$, $y(s_2)$ are three points on the spiral related according to the following equations $s_1 = \Psi(s_2 - s_0) + s_0$ when $s_0 \leq s_2 - s_0 + 2\pi$, $s_1 = \Psi(s_0 - s_2) + s_2$ when $s_0 - 2\pi < s_2 < s_0$, and $\Psi$ is a function with the properties $\Psi(0)=0$; $0<\Psi'(t)<1$, $t\epsilon[0,2\pi]$; $u(s_0, s_2)$ is a unit vector perpendicular to the plane containing the points $y(s_0)$, $y(s_1)$, $y(s_2)$;

$\dot{y}(s):=dy/ds$;

$\ddot{y}(s):=d^2y/ds^2$;

(iii) find a line for each $u(s_0, s_2)$ which is obtained by intersecting the plane through $y(s_0)$ and perpendicular to the said vector $u(s_0, s_2)$ with the plane Π; and (iv) repeating steps (i-iii), and forming a family of lines from a collection of the lines so that an exact image is reconstructed using the lines.

19. The method of claim 18, further comprising the step of:

moving the object at a nonconstant speed through a rotating source and oppositely located detector to generate the variable pitch spiral scan.

20. The method of claim 18, further comprising the step of:

positioning the object in a stationary position within a coil stand; and generating the spiral scan from at least one source and at least one oppositely located detector located on the coil stand.

* * * * *

UNITED STATES PATENT AND TRADEMARK OFFICE
CERTIFICATE OF CORRECTION

| | | |
|---|---|---|
| PATENT NO. | : 7,280,632 B2 | Page 1 of 1 |
| APPLICATION NO. | : 11/239605 | |
| DATED | : October 9, 2007 | |
| INVENTOR(S) | : Alexander Katsevich et al. | |

It is certified that error appears in the above-identified patent and that said Letters Patent is hereby corrected as shown below:

Please insert, col. 1, line 21;

-- STATEMENT REGARDING FEDERALLY SPONSORED RESEARCH OR DEVELOPMENT

This invention was funded in part by National Science Foundation, grant number DMS0104033. --

Signed and Sealed this
First Day of November, 2011

David J. Kappos
*Director of the United States Patent and Trademark Office*